United States Patent [19]
Phillips et al.

[11] Patent Number: 5,389,381
[45] Date of Patent: Feb. 14, 1995

[54] LYOPHILIZED POLYETHYLENE OXIDE MODIFIED PROTEIN AND POLYPEPTIDE COMPLEXES WITH CYCLODEXTRIN

[75] Inventors: Christopher P. Phillips, Brandamore; Robert A. Snow, West Chester, both of Pa.

[73] Assignee: Sterling Winthrop Inc., Malvern, Pa.

[21] Appl. No.: 178,205

[22] Filed: Jan. 5, 1994

Related U.S. Application Data

[62] Division of Ser. No. 23,182, Feb. 25, 1993, Pat. No. 5,298,410.

[51] Int. Cl.$^6$ .............. C12N 9/96; A61K 31/715; A61K 37/26
[52] U.S. Cl. .................. 424/94.3; 435/25; 435/188; 435/189; 435/192; 424/78.05; 424/78.31; 514/58; 530/410; 536/103
[58] Field of Search .............. 424/94.3, 78.05; 514/58; 530/410; 536/103; 435/25, 188, 189, 192

[56] References Cited

U.S. PATENT DOCUMENTS

| | | |
|---|---|---|
| 4,179,337 | 12/1979 | Davis et al. |
| 4,596,795 | 6/1986 | Pitha . |
| 4,727,064 | 2/1988 | Pitha . |
| 4,983,586 | 1/1991 | Bodor . |
| 5,006,333 | 4/1991 | Saifer et al. ............ 435/180 |
| 5,298,410 | 3/1994 | Phillips et al. ............ 435/188 |
| 5,334,382 | 8/1994 | Phillips et al. ............ 424/94.3 |

OTHER PUBLICATIONS

Anti-Inflammatory & Pharmacokinetic Properties of Superoxide Dismutase Derivatized with Polyethylene Glycol via Active Esters, Veronese et al, 1983 J. Pharm. Pharmacol. 35, 757–758.

Japanese Patent Application Publication 1–96, 107 (Kokai).

*Primary Examiner*—Herbert J. Lilling
*Attorney, Agent, or Firm*—Imre Balogh

[57] ABSTRACT

Disclosed are lyophilized biologically active proteinaceous compositions containing low diol polyalkylene oxide, such as polyethylene glycol, covalently attached to a biologically active proteinaceous substance and combined with the cryoprotectant cyclodextrin.

10 Claims, No Drawings

LYOPHILIZED POLYETHYLENE OXIDE MODIFIED PROTEIN AND POLYPEPTIDE COMPLEXES WITH CYCLODEXTRIN

This application is a division of application Ser. No. 08/023,182, filed on Feb. 25, 1993, now U.S. Pat. No. 5,298,410.

BACKGROUND OF THE INVENTION

1. Field of the Invention

This invention relates to lyophilized aqueous parenteral solutions of physiologically active proteins and polypeptides attached to low diol polyalkylene oxide combined with the cryoprotectant cyclodextrin.

More particularly, this invention relates to a lyophilized aqueous parenteral solution of superoxide dismutase attached to low diol polyethylene glycol combined with the cryoprotectant cyclodextrin.

2. Reported Developments

Biologically active proteins, particularly enzymes and peptide hormones, have been long considered as ideal drugs for the treatment of various diseases due to their specificity and rapid catalytic action. Such enzymes include:

Oxidoreductases such as: Urate: oxygen oxidoreductase (1.7.3.3; "uricase"); Hydrogen-peroxide: hydrogen-peroxide oxidoreductase (1.11.1.6; "catalase"); Cholesterol, reduced-NADP: oxygen oxidoreductase (20-$\beta$-hydroxylating) (1.14.1.9; "Cholesterol 20-hydroxylase").

Transferases such as: UDP glucuronate glucuronyl-transferase (acceptor unspecific) (2.4.1.17; "UDP glucuronyltransferase"); UDP glucose: $\alpha$-D-Galactose-1-phosphate uridylyltransferase 2.7.7.12).

Hydrolases such as: Mucopeptide N-acetylmuramyl-hydrolase (3.2.1.17; lysozyme); Trypsin (3.4.4.4); L-Asparagine aminohydrolase (3.5.1.1; "Asparaginase").

Lyases such as: Fructose-1,6-diphosphate D-glyceraldehyde-3-phosphate-lyase (4.1.2.12; "aldolase").

Isomerases such as D-Xylose ketol-isomerase (5.3.1.5; xylose isomerase) and

Ligases such as: L-Citrulline: L-aspartate ligase (AMP) (6.3.4.5).

The peptide hormones include:

Insulin, ACTH, Glucagon, Somatostatin, Somatotropin, Thymosin, Parathyroid hormone, Pigmentary hormones, Somatomedin, Erythropoietin, Luteinizing hormone, Chorionic Gonadotropin, Hypothalmic releasing factors, Antidiuretic hormones, Thyroid stimulating hormone, Calcitonin and Prolactin.

Therapy with physiologically active proteinaceous substances, particularly with non-human enzymes, has been less than successful due in part to their relatively short half-lives and to their respective immunogenicities. Upon administration, the host defense system responds to remove the foreign enzymes by initiating the production of antibodies, thereby substantially reducing or eliminating their therapeutic efficacies. Repeated administration of foreign and of otherwise short lived human enzymes is essentially ineffective, and can be dangerous because of concomitant allergic response. Various attempts have been taken to solve these problems, such as through microencapsulation, entrapment in liposomes, genetic engineering and attachment of the enzymes to polymers. Among the attempts the most promising appears to be the chemical attachment of the proteinaceous substances to polyalkylene oxide (PAO) polymers and particularly polyethylene glycols (PEG). The following illustrates these attempts.

U.S. Pat. No. 4,179,337 discloses the use of polyethylene glycol or polypropylene glycol coupled to proteins to provide a physiologically active non-immunogenic water soluble polypeptide composition in which the polyethylene glycol (hereinafter sometimes referred to as PEG) serves to protect the polypeptide from loss of activity without inducing substantial immunogenic response. The methods described in the patent for the coupling of polyethylene glycol to a protein involve either the conversion of a protein amino group into an amide or pseudoamide, with consequent loss of charge carrying capacity of the amino group, or the introduction at the amino group of the protein, or vicinal to it, of a heteroatom substituent such as a hydroxyl group or of a ring system that is not repeated in the polymer backbone.

Veronese, F. M., Boccu, E., Schaivon, O., Velo, G. P., Conforti, A., Franco, L., and Milanino, R., in *Journal of Pharmacy and Pharmacology*, 35, 757–758 (1983), reported that when bovine erythrocyte derived superoxide dismutase is modified with a polyethylene glycol carboxylic acid N-hydroxysuccinimide active ester, the half-life of the enzyme in rats is increased over that of the unmodified protein.

European Patent Application 0 200 467 of Anjinomoto, Inc. describes superoxide dismutase that is chemically modified by a polyalkylene oxide (PAO) which is functionalized at both ends of the polymer with activated carboxyl coupling groups, each capable of reacting with protein. Because the activated coupling sites are located at opposite ends of the polymer chain, it is unlikely that the presence of an activated group at one end of the polymer can have a significant effect on the reactive nature of the group at the other end of the polymer. These polymers are capable of reacting at both ends to cross-couple with proteins to form copolymers between the protein and the polyalkylene oxide. Such copolymers do not have well defined or molecularly stoichiometric compositions.

Veronese, F. M. et al in *Journal of Controlled Release*, 10,145–154 (1989) report that the derivatization with monomethoxypolyethylene glycol (hereinafter sometimes referred to as MPEG) of superoxide dismutase (hereinafter sometimes referred to as SOD) gives a heterogenous mixture of products. Heterogeneity was demonstrated to depend on the presence of bifunctional polyethylene glycol (DPEG) in the monofunctional methoxylated molecules.

These attempts, in general, have resulted in somewhat longer half-life and reduced immunogenicity of the proteinaceous physiologically active substances. However, it appears that further improvements are necessary to successfully treat a variety of diseases with these promising biological substances.

In co-pending patent application Serial No. 07/936,416 (which is incorporated herein by reference) it is disclosed that biologically active proteinaceous substances can be made to possess longer half-life and less immunogenic properties by chemically modifying them using low diol polyalkylene oxide, preferably polyethylene glycol. The formulations disclosed have distinct advantages over the prior art disclosed formulations of polyethylene glycol-modified, proteinaceous substances.

During storage in the liquid state, polyethylene glycol proteinaceous molecules are hydrolyzed to a mixture of free polyethylene glycol, polyethylene glycol-protein and succinate-protein moieties. To prevent such a destabilization process, the formulations may be lyophilized. With lyophilization, however, the concentration of protein and stabilizers is at high levels and, depending on the excipients employed, deleteriously influence the degree of intermolecular aggregation that occurs during storage.

It has been found that cyclodextrins inhibit the rate of intermolecular aggregation of covalently attached low diol polyethylene glycol-proteins during their storage, and therefore, provide for extended shelf-life.

Cyclodextrins are known in the art to possess the ability to form inclusion complexes and to have concomitant solubilizing properties. Derivatives of cyclodextrins are also known to possess these properties. Their use is illustrated by the following patents.

U.S. Pat. No. 4,596,795, relates to the administration of sex hormones in the form of their complexes with hydrophilic derivatives of cyclodextrin, such as poly-β-cyclodextrin and hydroxypropyl-β-cyclodextrin, by sublingual or buccal routes. The complexes were found highly water-soluble and effective by comparison to other cyclodextrin derivatives.

U.S. Pat. No. 4,727,064 discloses pharmaceutical preparations consisting of a drug having low water solubility and an amorphous water-soluble cyclodextrin-based mixture. The addition of the cyclodextrin-based mixture improves the dissolution properties of the drug. The cyclodextrin-based mixture is prepared from α-, β-or γ-cyclodextrin which were rendered amorphous through non-selective alkylation.

International Application No. PCT/US89/04099 (WO 90/03784) describes a lyophilized composition comprising a polypeptide and a stabilizing/solubilizing amount of cyclodextrin selected from the group consisting of hydroxypropyl, hydroxyethyl, glucosyl, maltosyl and maltotriosyl derivatives of β- and γ-cyclodextrin.

U.S. Pat. No, 4,983,586 discloses a method for decreasing the incidence of precipitation of a lipophilic and/or water-labile drug occurring at the injection site, when the drug is being parenterally administered, comprising administering the drug in an aqueous solution containing about 20% to 50% hydroxypropyl-β-cyclodextrin.

A large number of drugs are claimed including: antineoplastics, sedatives, tranquilizers, anticonvulsants, antidepressants, hypnotics, muscle relaxants, antispasmodics, anti-inflammatories, anticoagulants, cardiotonics, vasodilators and anti-arrhythmics.

We have surprisingly found that lyophilized parenteral formulations comprising conjugated low diol polyoxyethylene oxide and a physiologically active protein or polypeptide in a complex with cyclodextrin provide stability on extended shelf-life to the formulations without intramolecular aggregation.

SUMMARY OF THE INVENTION

Accordingly, the present invention provides stable parenteral formulations of physiologically active proteins covalently bound to low diol polyalkylene oxide (hereinafter sometimes referred to as LDPAO), preferably low diol polyethylene glycol (hereinafter sometimes referred to as LDPEG) complexed with cyclodextrins.

More specifically, the present invention is directed to a pharmaceutical composition comprising:

from about 150 to about 150,000 U/ml, preferably,
from about 25,000 to about 150,000 U/ml, most preferably,
from about 50,000 to about 150,000 U/ml of a covalently bound low diol polyethylene oxide/protein;
from about 0.1 to about 20% w/v, preferably,
from about 1.0 to about 15% w/v, and most preferably,
from about 5 to about 10% w/v of cyclodextrin; and
from about 0.01 to about 50 mM of a buffer at a pH of 5.7 to 6.5.

As used herein, the term "low diol" with respect to a polyalkylene oxide, such as polyethylene glycol, refers to a linear polyalkylene oxide containing not more than about 10% of non-monoalkoxylated polyalkylene oxide, preferably non-monomethoxylated polyethylene glycol.

The preferred low diol polyethylene oxide used in the present invention is a polyethylene glycol polymer having average molecular weights of from about 1,000 to about 15,000 daltons and containing not more than about 10% w/w of non-monomethoxylated polyethylene glycol are especially suitable for covalent attachment to biologically active proteins, especially to superoxide dismutase. More preferably, polyethylene glycols having average molecular weights of from about 2,000 to about 10,000 daltons and most preferably of from about 4,000 to about 6,000 daltons are used in the present invention wherein the polyethylene glycol preferably contains less than about 7% w/w and most preferably less than about 5% w/w non-monomethoxylated polyethylene glycol.

The biologically/physiologically active proteins, polypeptides and hormones used in the present invention include:

Recombinant human interleukin-4 (rhuIL-4);
Protease Subtilisin Carlsberg;
Superoxide dismutases such as bovine, human, and various recombinant superoxide dismutases such as recombinant human superoxide dismutase (rhuSOD);
Oxidoreductases such as: Urate: oxygen oxidoreductase (1.7.3.3; "uricase"); Hydrogen-peroxide: hydrogen-peroxide oxidoreductase (1.11.1.6; "catalase"); Cholesterol, reduced-NADP: oxygen oxidoreductase (20-β-hydroxylating) (1.14.1.9; "Cholesterol 20-hydroxylase");
Transferases such as: UDP glucuronate glucuronyltransferase (acceptor unspecific) (2.4.1.17; "UDP glucuronyltransferase"); UDP glucose: α-D-Galactose-1-phosphate uridylyltransferase 2.7.7.12);
Hydrolases such as: Mucopeptide N-acetylmuramylhydrolase (3.2.1.17; lysozyme); Trypsin (3.4.4.4); L-Asparagine aminohydrolase (3.5.1.1; "Asparaginase ");
Lyases such as: Fructose-1,6-diphosphate D-glyceraldehyde-3-phosphate-lyase (4.1.2.12; "aldolase");
Isomerases such as D-Xylose ketol-isomerase (5.3.1.5; xylose isomerase); and
Ligases such as: L-Citrulline: L-aspartate ligase (AMP) (6.3.4.5).

Insulin; ACTH; Glucagon; Somatostatin; Somatotropin; Thymosin; Parathyroid Hormone; Pigmentary Hormones; Somatomedin; Erythropoietin; Luteinizing Hormone; Chorionic Gonadotropin; Hypothalmic Releasing Factors; Antidiuretic Hormones; Thyroid Stimulating Hormone; Calcitonin; Prolactin; Interferons (alpha, beta and gamma); Antibodies (IgG, IgE, IgM, IgD); Interleukins 1, 2, 3, 4 and 7; Granulocyte Colony Stimulating Factor (GCSF); Granulocyte-Macrophage Colony Stimulating Factor (GM-CSF); Tumor Necrosis Factor (TNF); Platelet Derived Growth Factor (PDGF); Epidermal Growth Factor (EGF); Nerve Growth Factor (NGF); Bone Growth Factor (BGF); Growth Hormone Releasing Factor (GHRF); Papain; Chymotrypsin; Thermolysin; Streptokinase and Activase.

Cyclodextrins used in the present invention are $\alpha$-, $\beta$-and $\gamma$-cyclodextrins composed of 6, 7 and 8 glucose units respectively. They are known in the art and recognized to possess the ability to form inclusion complexes with certain drugs, proteins and polypeptides and to have concommitant solubilizing properties.

The inside cavity of cyclodextrin is lipophilic, while the outside of the cyclodextrin is hydrophilic. Because of these properties they have been used in forming inclusion complexes with pharmaceuticals. For the purpose of stabilizing the low diol polyalkylene oxide/protein conjugates hydroxyethyl, hydroxypropyl, glucosyl, maltosyl and maltotriosyl derivatives of $\beta$-cyclodextrin are especially suitable.

The pharmaceutically acceptable aqueous carrier utilized by the present invention is a non-toxic, inert medium in which is dissolved the complex of cyclodextrin low diol polyethylene oxide/peptide conjugate and a pharmaceutically acceptable buffer, such as sodium phosphate, sodium acetate, sodium carbonate and those derived from mineral and organic acids. By pharmaceutically acceptable buffers it is meant that the buffers are relatively innocuous to the mammalian organism in medicinal doses of the buffers so that the beneficial properties of the active complex are not vitiated by side effects ascribable to the buffers.

DETAILED DESCRIPTION OF THE INVENTION

In the process of making the formulations of the present invention, first, the low diol polyethylene glycol is covalently attached to the biologically active protein as shown schematically:

a) LDPEG+carboxylating agent→LDPEG-COOH b) LDPEG-COOH+carboxyl group activating agent→active ester of LDPEG-COOH c) n (active esters of LDPEG-COOH)+Protein→(LDPEG-CO)$_n$-Protein wherein:

LDPEG-COOH is LDPEG carboxylated at hydroxyl sites; and n is the number of sites of attachment of LDPEG to protein.

LDPEG is carboxylated at the hydroxyl sites, then the carboxyl groups are esterfied with a carboxyl activating agent to form the active esters which are then coupled to the protein molecule. The number of LDPEG molecules attached to the protein will vary according to the number of reactive groups, such as amino groups, present on the protein molecule.

The LDPEG is then dissolved in a pharmaceutically acceptable aqueous carrier, followed by the addition and dissolution of the desired cyclodextrin. The solution is then freeze-dried in a lyophilizer. The lyophilized solution is reconstituted with sterile water prior to its administration to the patient.

The invention will be described with specific reference to superoxide dismutase (hereinafter sometimes referred to as SOD).

Superoxide dismutase is an intracellular enzyme present in all oxygen-metabolizing cells and is responsible for catalyzing the conversion of the superoxide radical to oxygen and hydrogen peroxide. The superoxide radical and species derived from it are believed to be causative agents in a wide variety of inflammatory disorders. Superoxide dismutase is being used to treat certain inflammatory conditions under the tradename of Orgotein. In addition, the use of SOD has been investigated for broncho-pulmonary dysplasia and hyperbaric oxygen toxicity, acute inflammation caused by burns and infections, reperfusion injury following organ transplants, retrolental fibroplasia, side effects of therapeutic ionization radiation and certain dermatological conditions. However, when SOD is administered by intravenous injection to a mammal, the enzyme's half-life is only a few minutes and it disappears from circulation. As a result, the enzymatic activity is not sufficient to remove toxic substances from the bloodstream. Repeated administration on the other hand causes adverse reactions.

Low diol polyalkylene oxide comprising chains of polyalkylene oxide of varying molecular weight and containing at least one hydroxyl group per chain, such as low diol polyethylene glycol (LDPEG) is attached to superoxide dismutase (SOD) to form a biologically active composition having longer half-life and less immunogenicity than either native SOD or a PAO-SOD composition. Upon lyophilization, LDPEG forms undesirable aggregates which affect its biological activity. Its complexation with cyclodextrin eliminates aggregate formation and the reconstituted formulation is rendered stable on extended shelf-life.

The process of attaching LDPEG to SOD (sometimes hereinafter referred to as LDPEGation) comprises the steps of:

activating low diol methoxy-PEG, having an average molecular weight of from about 1,000 to about 15,000, more preferably of from about 2,000 to 10,000, and most preferably from about 4,000 to 6,000 daltons, containing not more than about 10% non-monomethoxylated PEG, by succinylation to form LDPEG-succinate (LDPEG-S), preferably with succinic anhydride (SA), followed by the formation of a reactive ester, preferably with N-hydroxy succinimide (NHS), to form LDPEG-SS, and then reacting of LDPEG-SS with an accessible reactive site on SOD, preferably a primary amine residue on SOD, mainly lysine epsilon amine. Referring specifically to LDPEG-SOD, the process is as shown:

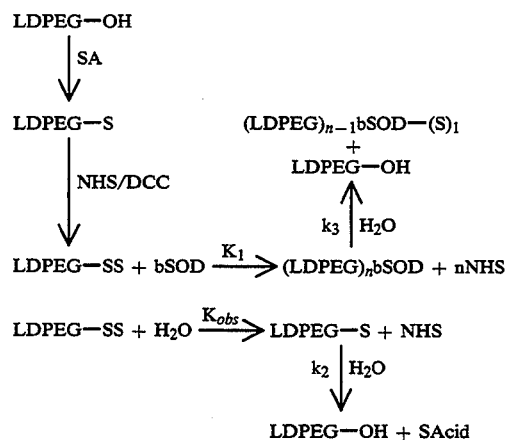

wherein:

LDPEG—OH=low diol CH$_3$O—PEG—OH containing not more than about w/w of HO—PEG—OH LDPEG—SS=low diol CH$_3$O—PEG—OCOCH$_2$CH$_2$COO(C$_4$H$_4$NO$_2$) containing not more than 10% of [(C$_4$H$_4$O$_2$N)OOC—CH$_2$CH$_2$COO]$_2$PEG LDPEG—S=low diol CH$_3$O—PEG—OCOCH$_2$CH$_2$COOH containing not more than 10% of [HOOC—CH$_2$CH$_2$—COO]$_2$PEG DCC=dicyclohexylcarbodiimide SA=succinic anhydride bSOD=Bovine Superoxide Dismutase NHS=(C$_4$H$_4$NO$_2$)OH, N-hydroxysuccinimide (LDPEG)$_n$bSOD=low diol(CH$_3$O—PEG—OCOCH$_2$CH$_2$CO)$_n$—bSOD (LDPEG)$_{n-1}$bSOD—S=low diol(CH$_3$O —PEG—OCOCH$_2$CH$_2$CO)$_{n-1}$—bSOD—COCH$_2$CH$_2$COOH SAcid=Succinic Acid n=number of low diol PEGs per SOD K$_1$, K$_{obs}$, k$_2$ and k$_3$ are rate constants for the reactions.

Essential components used in the formulations of the present invention will now be described.

Starting Materials, Intermediates and Reagents

Superoxide Dismutase

Superoxide dismutase is the name given to a class of enzymes that catalyze the breakdown of the superoxide anion radical (O$_2$$^-$·) to oxygen and hydrogen peroxide. SOD is known under the systematic nomenclature of the International Union of Biochemistry as superoxide oxidoreductase and has a classification number of 1.15.1.1. Such substances have been called orgoteins and hemocupreins as well as superoxide dismutases and range in molecular weight from about 4,000 to about 48,000. The copper-zinc dismutases are a remarkably conserved family with respect to gross structural properties. Without exception, the purified enzymes have been shown to be dimers (molecular weight usually 31,000-33,000) containing two moles each of copper and zinc ions per mole. The enzymes of the manganese/iron family are not as uniform in such basic properties as molecular weight, subunit structure and metal content. Some are dimers; others are tetramers. The content of metal ranges from about 0.5 to 1 mole per mole of subunit polypeptide chain. Naturally occurring Zn/Cu-containing enzymes from mammals and their functionally competent analogs and muteins are considered to be mammalian Zn/Cu superoxide dismutases (mSOD).

In formulations of the present invention mSOD may be of any origin. It is commercially obtained from bovine erythrocytes and human erythrocytes as well as by recombinant synthesis in microorganisms, such as *E-coli* and yeast. Among other sources, Cupri-Zinc bovine liver superoxide dismutase (SOD, EC 1.15.1.1) for example, is available from DDI Pharmaceuticals, Inc. (Mountain View, Calif.).

Polyethylene Glycol

In practicing the present invention, we prefer to use low diol PEG for attachment to biologically active proteins. While certain molecular weight methoxypolyethylene glycols are available commercially (for example, methoxy-PEG$_{5,000}$ was obtained from Union Carbide Corporation in two forms: a conventionally available high diol methoxy-PEG$_{5,000}$ which contained 14-17% of higher molecular weight PEG diol, and a low diol product which contained less than 4% PEG diol) some are required to be made and purified in order to produce a pegated protein that possesses low immunogenicity. For example, pegation of SOD with methoxy-PEG—SS derived from some commercial sources leads to a product containing high molecular weight components, as verified by size exclusion chromatography, discussed earlier. This high molecular weight product is believed to derive from protein cross-linking through an activated diester formed from the various amounts of PEG diol found in the commercial sources of M—PEG. The individual active esters, although located on the same polymer chain, are nonetheless chemically remote from one another. Thus, the presence of a second reactive functionality in the polymer tends to exert an increasingly negligible effect on the reactivity of a first reactive functionality as the distance separating the two functionalities increases. The individual reactivities thus tend to be independent of moieties present at opposite ends of the polymer chain, and crosslinking cannot be avoided in the absence of infinite dilution of reagents. It is, accordingly, important to synthesize an M—PEG—SS known to contain very small amounts, preferably no amounts of diester. S. Zalipsky et al in the *Journal of Bioactive and Compatible Polymers*, Vol. 5, April 1990, pp. 227-231, described the purification of polyethylene glycol 2000 from methoxypolyethylene glycol 2000. The succinate esters are also prepared and shown to separate by ion exchange chromatography on DEAE-Sephadex. The preparative method is shown in Example 3.

While the procedure described in Example 4 works well with PEG-2000, it fails with higher molecular weight PEG's. Higher molecular weight PEG acids do not bind to anion or cation resins; the greater mass of polyethylene backbone is believed to mask any ionic properties of the pendant acid. We have found that extremely low ionic strength buffer was required to bind the PEG succinates and they eluted under very low increases of ionic strength indicating that they are only very weakly held by the resin.

We have found that higher molecular weight methoxy-PEGs can be separated from diol components if the hydroxyl functionalities are first converted to dimethoxytrityl (DMT) ethers before application of reverse phase thin layer chromatography. The hydroxyls can be liberated by acid treatment.

The schematics of preparation and purification of methoxy-PEG$_{5000}$-dimethoxytrityl (M—PEG—DMT) derivatives are as follows; while the details are shown in Examples 4 through 7.

M—PEG—DMT and DMT—PEG—DMT are prepared in an identical fashion. The polyether is dissolved in ethanol-free chloroform and the solution dried by distilling off approximately half the chloroform at atmospheric pressure under a blanket of argon. The solution is then allowed to cool to room temperature under argon, followed by the sequential addition of excess diisopropylethyl amine (1.5 eq.), 10 mol % 4-dimethylaminopyridine as catalyst, and finally an excess amount of 4,4-dimethoxytrityl chloride (1.2 eq.). After 15 hours reaction, the solution is concentrated by rotary evaporation and the solution added to anhydrous ether to precipitate the tritylated PEG. Regular phase TLC cleanly separates starting material from product, the PEG backbone staining with Dragendorf's reagent. While M—PEG—DMT is not resolved from DMT—PEG—DMT by regular phase TLC, reverse phase C-18 TLC plates cleanly separate M—PEG—DMT, DMT—PEG—DMT, DMT chloride and DMT alcohol from each other (mobile phase 4:1:1 acetonitrile/water/isopropanol). PEG backbone is confirmed by staining orange to Dragendorf's and trityl incorporation confirmed by exposing the plate to HCl vapors to give an orange stain.

Authentic M—PEG—DMT 5000 was shown to separate cleanly from authentic DMT—PEG—DMT 8000 on a Waters C-8, 300 angstrom pore size, 15-20 micron particle size Prep-Pak Bondapak cartridge. The crude M—PEG—DMT was dissolved by sonication in 30% acetonitrile/water to a concentration of approximately 12 mg/ml and passed through a 2.5 micron filter. The sample was loaded onto the column (2 g in 25 ml) in a 30% acetonitrile/water mobile phase. After 8 minutes of isocratic elution, a contaminating peak eluted (identity unknown, having a high absorbance at 280 nm but accounting for very low relative mass). A gradient of 30-70% acetonitrile/water over 21 minutes was then begun, and the desired M—PEG—DMT eluted at 58-60% acetonitrile. Authentic DMT—PEG—DMT typically elutes at 80% acetonitrile. The first $\frac{3}{4}$ of the desired peak is collected and the last $\frac{1}{4}$ discarded. In this way, 15.4 g of M—PEG—DMT was purified from 22.6 g of crude M—PEG—DMT.

The trityl cleavage of M—PEG—DMT is as follows: attempted removal of the DMT group from M—PEG—DMT with HCl gave by TLC (crude undiluted reaction mixture) complete removal of the trityl group. However, concentration of the chloroform extract gave a back reaction which resulted in a re-tritylation of a significant portion of the PEG. It was not possible to purify this by selective precipitation. The hydrated trityl cation and chloride are apparently in equilibrium with the result that dehydration, such as occurs during solvent removal, produces significant quantities of DMT chloride. This re-tritylation may be prevented by the use of a non-equilibrating counterion. Sulfuric acid was shown to irreversibly de-tritylate M—PEG—DMT. The sulfuric acid cleaved M—PEG is extracted into chloroform, concentrated and precipitated into ether to give pure zero diol M—PEG. In this manner, 10 g of M—PEG—DMT was cleaved to 8.68 g of zero diol M—PEG. Size exclusion chromatography indicates this material contains less than 0.3% diol.

Other higher molecular weight methoxy-PEG derivatives can be made by analogous processes.

The following examples will serve better to illustrate preparation of the low diol PEG/proteinaceous conjugates to form a complex with cyclodextrin.

EXAMPLE I

A. Methoxypolyethylene Glycol Succinate (M—PEG—S)

In a 2 liter flask, 100 g (0.02 mole) of methoxy-PEG$_{5,000}$(M—PEG) was dissolved with stirring in 300 ml of warm (40° C.) anhydrous toluene. The volume was reduced by azeotropic removal of 147 ml of toluene under a nitrogen atmosphere to reduce the water content of the m-PEG from 1.73 to 0.23%. After cooling to ambient temperature, 233 ml of dry methylene chloride followed by 3.0 g (0.09 moles) of succinic anhydride and 1.1 g (0.01 mole) of 4-dimethylaminopyridine (DMAP) were added. The reaction was stirred and heated at reflux overnight, and then 200 ml of methylene chloride was removed at reduced pressure. The residue was added with stirring to 1.6 liters of ether in a 4 liter flask. This was stirred for 45 minutes and filtered. The filter cake was washed with 70 ml of ether and dried at reduced pressure to afford 100.4 g of crude m-PEG-succinate (m—PEG—S) as a white solid containing DMAP.

The crude M—PEG—S (100 g) was dissolved in 633 ml of methylene chloride and passed through a column containing 114 g of Dowex 50x8-100H+ resin previously washed with 272 ml dioxane followed by 316 ml of dry methylene chloride. The column was then washed with an additional 316 ml of methylene chloride, and the eluents were combined and dried over anhydrous magnesium sulfate. Methylene chloride (800 ml) was removed under reduced pressure. The remaining solution was added with stirring to 1600 ml of ether in a 4000 ml flask. After stirring for 30 minutes, the suspension was allowed to stand for 30 minutes and then filtered. The filter cake was then washed with 75 ml of ether and dried at reduced pressure. This afforded 96.0 g (94% yield) of m—PEG—S as a white solid which exhibited a proton NMR spectrum consistent with the assigned structure: $^{1}$H—NMR (CDCl$_3$): 4.27 (triplet, 2H, —C$\underline{H}_2$—O—C(=O)—), 3.68 (large singlet offscale, PEG methylene O—C$\underline{H}_2$—'s), 3.39 (singlet, 3H, OC$\underline{H}_3$), and 2.65 ppm (narrow multiplet, 4H, —C(=O)—C$\underline{H}_2$—C$\underline{H}_2$—C(=O)—). The carboxylic acid content of 0.000207 mol/g was measured by titration.

B. Methoxypolyethylene Glycol N-Succinimidyl Succinate (M—PEG—SS)

In a 2,000 ml flask, 98.48 g (0.0192 mole) of methoxypolyethylene glycol succinate (m—PEG—S) was dissolved in 468 ml of dry toluene with warming to 40° C. The solution was filtered and the volume was reduced by 263 ml by azeotropic distillation under nitrogen. The resultant viscous liquid was transferred to a 1,000 ml three-necked flask under nitrogen using 225 ml of dry methylene chloride. To this was added 2.22 g (0.0192 mole) of N-hydroxysuccinimide, and the reaction was stirred until the N-hydroxysuccinimide dissolved. The reaction mixture was then cooled to 5° C. in an ice bath, and a solution of 4.44 g (0.0125 mole) of dicyclohexylcarbodiimide (DCC) in 24 ml of methylene chloride was added dropwise over 5 minutes. During the addition of the methylene chloride/DCC solution, dicyclohexylurea (DCU) began to crystallize from the reaction mixture. The reaction was allowed to warm to room temperature and was stirred overnight. The content of the reaction flask was transferred to a 2,000 ml flask using 25 ml of methylene chloride to rinse the flask. At reduced pressure at 30° C., 250 ml of methylene chloride was removed, the suspension was filtered and the filter cake was washed with 25 ml of dry toluene. The filtrate was then added to 1,200 ml of anhydrous ether with stirring, and the resultant suspension was stirred for 45 minutes before being filtered. The filter cake was rinsed with 100 ml of dry ether and dried under a latex rubber dam for 2 hours. The resultant solid was then dried under high vacuum and transferred to a bottle in a glove bag under argon. This afforded 96.13 g (96.1% yield) of the title compound (m—PEG—SS) as a white solid which exhibited a proton NMR spectrum consistent with the assigned structure: $^{1}$H—NMR (CDCl$_3$): 4.32 (triplet, 2H, —C$\underline{H}_2$—O—C(=O)—), 3.68 (large singlet offscale, PEG methylene O—C$\underline{H}_2$—'s), 3.39 (singlet, 3H, OC$\underline{H}_3$), 2.99 and 2.80 (pair of triplets, each 2H, succinate-C(=O)—C$\underline{H}_2$C$\underline{H}_2$—C(=O)—), and 2.85 ppm (singlet, 4H, succinimide —C(=O)—C$\underline{H}_2$C$\underline{H}_2$—C(=O)—). The active ester content of the product was determined by reaction with excess benzylamine in toluene followed by back titration with perchloric acid in dioxane to a methyl red end-point and found to be 0.000182 mole/g.

C. Low Diol PEG—SOD 11.8 g of an aqueous solution of SOD containing 82.1 mg of protein per gram was diluted to a total weight of 200 g with 0.1M sodium phosphate buffer at pH 7.8. To this solution, magnetically stirred and heated to 30° C., was added 3.4 g of low diol methoxy PEG—SS prepared in Example 1B. The pH of the reaction mixture was maintained at 7.8 using a Mettler DL25 titrator programmed in the pH stat mode to add 0.5 normal sodium hydroxide solution as required. After 1 hour the reaction mixture was filtered through a 0.2 micron low protein binding polysulfone filter, concentrated to about 60 ml using a stainless steel Millipore Mini-tan device equipped with a 30,000 NMWL membrane 4 pk and was then subjected to dialfiltration against 2 liters of 50 mM sodium phosphate buffered saline (0.85%) at pH 6.2 to 6.3. The retentate solution containing the low diol PEG—SOD was then filtered through a 0.2 micron filter.

EXAMPLE 2

A. Monomethoxypolyethylene glycol succinate

A 12 liter three-neck flask was charged with 4 liters of toluene and 2212 g of methoxypolyethylene glycol, previously warmed to 70° C. under nitrogen. The volume was reduced by azeotropically removing 1.3 liters of toluene at reduced pressure. After cooling to 30° C., there was added 4 liters of methylene chloride followed by 66.4 g of succinic anhydride and 24.4 g of 4-dimethylaminopyridine. The reaction was refluxed for 32 hours then 3.8 liters of methylene chloride was removed at atmospheric pressure. The reaction was cooled and poured into a 5 gal. glass carboy containing 28 liters of methyl tert-butyl ether with stirring. The resulting suspension was stirred for 1 hour and collected on a Lapp filter. The filter cake was washed with 1 liter of methyl tert-butyl ether. Drying in a vacuum overnight at room temperature yielded 2.252 kg of the title compound as a crude white solid.

The crude title compound was dissolved in 8 liters of methylene chloride and passed through a glass pressure column containing 3.0 kg of Dowex 50W-X8 resin (cation exchange, hydrogen form) previously washed with 5 liters acetone followed by 4 liters of methylene chloride. The column was then washed with 3 liters of methylene chloride. The column eluents were combined and 10 liters of methylene chloride was removed at atmospheric pressure. The remaining solution was poured into 26 liters of methyl tert-butyl ether with stirring. The resulting suspension was stirred for 45 minutes and the solid was removed by filtration. This was washed with 3 liters of methyl tert-butyl ether. Drying in a vacuum oven at room temperature yielded 2.46 kg of a white solid of the title compound, 95% recovery. This material contained 1.5% methoxypolyethylene glycol, and assayed at $2.72 \times 10^{-4}$ mole/g (theory is $1.96 \times 10^{-4}$ mole/g).

B. Methoxypolyethylene glycol N-succinimidyl succinate

In a 12 liter flask under nitrogen 1.5 kg of monomethoxypoly ethylene glycol succinate was dissolved in 7.2 liters of toluene with warming. The volume was reduced by 2.8 liters at reduced pressure to remove water. The resultant viscous liquid was cooled to 40°–45° C. and 3.4 liters of methylene chloride was added followed by 33.89 g of N-hydroxysuccinimide. The reaction was stirred for 1 hour until all the N-hydroxysuccinimide was dissolved, then the reaction was cooled to 10° C. and a methylene chloride solution (368 ml) of 67.75 g 1,3-dicyclohexylcarbodiimide (DCC) was added dropwise over 30 minutes. The reaction was allowed to warm slowly to room temperature while being stirred over 18 hours. The volume was then reduced by 3.2 liters at atmospheric pressure. The suspension was cooled to 0°–5° C. and stirred for 30 minutes. This was filtered and the filter cake was washed with 250 ml of toluene. The filtrate and the wash was added to 28 liters of methyl tert-butyl ether with stirring. The resultant suspension was stirred for 45 minutes and then filtered on a Lapp filter. The filter cake was washed with 1 liter of methyl tert-butyl ether and dried under a latex dam for 4 hours. Additional drying at room temperature in a vacuum oven at reduced pressure overnight yielded 1.5 kg of a white solid, 100% yield. This material assayed at $1.79 \times 10^{-4}$ mole/g (theory is $1.92 \times 10^{-4}$ mole/g).

C. Methoxypolyethylene glycol succinoyl bovine superoxide dismutase

To 32 liters of warm (29°–30° C.) pH 7.8 phosphate buffer in a 42 liters reactor containing a pH electrode was added 194.0 g of bovine erythrocyte superoxide dismutase. The volume was adjusted to 39.5 liters and the reaction was warmed to 29° C. The sodium hydroxide tube from the pH titrator was adjusted over the center of the reactor directly above the surface of the solution. The pH titrator was initiated and the pH was adjusted to 7.8 with 0.5N sodium hydroxide. At this time 614.7 g of methoxypolyethylene glycol N-succinimidyl succinate was added over two minutes and the reaction was stirred for 41 minutes while the pH was being adjusted to 7.8 with 0.5N sodium hydroxide with the reaction temperature being maintained at 30° C. The reaction was then filtered through a 200 Millipak filter and concentrated using a Millipore stainless steel Pellicon diafiltration system. The reactor was then rinsed with 600 ml of pH 6.2 phosphate buffer. The rinse was added to the concentrate after filtering through the Millipore 200 filter and the dialfiltration system. The final volume of the concentrate was about 9 liters. The concentrate was then diafiltered, using the Millipore Pellicon diafiltration system against 200 liters of pH 6.2 phosphate buffer over 2.17 hours. The diafiltration system was rinsed with 1.5 liters of pH 6.2 phosphate buffer. The final volume of the concentrate was about 8 liters. The concentrate was then transferred to a clean 5 gal glass carboy through an inline Millipore 200 Millipak filter and the filter was rinsed with 500 ml of pH 6.2 phosphate buffer. This afforded 11.98 kg (91.4% yield) of the title compound as a clear greenish-blue solution. (Activity: 32,960 units/ml).

EXAMPLE 3

A. Preparation of partially carboxymethylated polyethylene oxide

Polyethylene oxide, $M_w 2000$ (Fluka, 25 g, 25 meq. OH) was dissolved in toluene (120 ml) and azeotropically dried until no more water appeared in the Dean-Stark trap attachment (approx. 25 ml of toluene were removed). The solution was cooled to 50° C. and treated with potassium tert-butoxide (1.7 g, 15 mmol). The solution was brought to reflux and more solvent was distilled off (approx. 25 ml). The stirred reaction mixture was brought to 25° C., and treated overnight with ethyl bromoacetate (3.4 ml, 16 mmol). The precipitated salts were removed by gravity filtration, and washed with methylene chloride (30 ml). The polymer was recovered by partially concentrating the filtrate (to approx. 60 ml), and slowly pouring the concentrated solution into ethyl ether (300 ml) at 5° C. with vigorous stirring. The collected white polymeric powder was dried in vacuo. Yield: 24 g; IR (neat) showed the characteristic ester absorption at 1753 cm[31 1]. The polymer was dissolved in 1N NaOH (50 ml), and NaCl (10 g) was added. After approx. 45 min this solution was acidified with 6N HCl to pH 3.0 and extracted with methylene chloride (3×60 ml). The combined organic phases were dried (MgSO$_4$), concentrated (to approx. 50 ml), and poured into cold stirring ether (300 ml). The precipitated product was collected by filtration and dried in vacuo. Yield: 22 g; IR (neat) showed absorption at 1730 cm$^{-1}$, corresponding to ω-carboxyl group.

B. Preparation of pure α-hydroxy-ω-carboxymethylpolyethylene oxide by separation of partially carboxymethylated PEO on DEAF-Sephadex The mixture of homo- and heterobifunctional PEO's (22 g) was dissolved in water (40 ml), and applied to a column containing DEAE-Sephadex A-25 (Sigma, 27 g, 0.1 mole ion-exchange sites) in the tetraborate form. The first fraction containing underivatized polymer was eluted with deionized water. When the eluent became negative to a PAA test, a stepwise ionic gradient of ammonium bicarbonate (from 6 to 22 mM at increments of 1-2 mM every 100 ml) was applied, and fraction collection (approx. 40 ml each) began. Fractions 2-21 were positive to the PAA test, and contained pure monocarboxylated PEO ($R_1$=0.49). The subsequent three fractions did not contain PEO, while fractions 25-36 contained the pure PEO-diacid ($R_1$=0.26). The fractions containing α-hydroxy-ω-carboxymethylpolyethylene oxide were combined and concentrated (to approx. 100 ml). Sodium chloride (35 g) was dissolved in this solution, which was then acidified to pH 3 and extracted with methylene chloride (3×100 ml). The combined CH$_2$Cl$_2$ solution was dried (MgSO4), concentrated (to approx. 100 ml), and slowly poured into cold stirring ether (500 ml). The precipitated polymer was collected and thoroughly dried in vacuo to give 8.8 g of product. $^{13}$C—NMR (CDCl$_3$): δ172.7 (COOH); 72.4 (CH$_2$CH$_2$OH); 70.4 (PEO); 69.0 (CH$_2$COOH); 61.3 (CH$_2$OH)ppm.

Bis-carboxymethylpolyethylene oxide isolated from the column was also analyzed. $^{13}$C—NMR (CDCl$_3$): δ172.4 (COOH); 70.4 (PEO); 68.8 (CH$_2$COOH) ppm.

EXAMPLE 4

Synthesis of Dimethoxytrityl Methoxypolyethylene Glycol

Methoxypolyethylene glycol (5,000 dalton average molecular weight; 36.3 g, 7.26 mmol) was dissolved in 500 ml chloroform, followed by the removal by distillation of 250 ml chloroform to remove water. A drying tube was attached to the flask and the solution allowed to cool to approximately 50° C. N,N-diisopropylethylamine (1.8 ml, 10.3 mmol) was added, followed by 4-dimethylamino pyridine (100 mg, 0.8 mmol, 10 mol %) and 2.9 g of 4,4-dimethoxytrityl chloride (98%).

The mix was allowed to stir overnight at room temperature at which time the solvent was removed by rotary evaporation at 60° C. The residue was taken up in a small amount of chloroform, and the M—PEG—DMT was precipitated by addition into 2 liters of anhydrous ether. The precipatate was collected, dried and chromatographed on a C-8 300A reverse phase prep column on a Waters LC4000 system employing a 30-95% acetonitrile gradient (against water) over 20 minutes. The desired product eluted at 58-60% acetonitrile. The sample (2 g) in 20 ml of 30% acetonitrile/water was loaded onto the column at 50 ml/min flow rate. This eluent (30% acetonitrile/water) was allowed to continue isocratically until a large impurity peak was eluted, typically 3-5 min, mv 280 μm. After the elution of this first peak, the gradient was started. The next peak to elute was the desired methoxy—PEG—DMT 5000. The first ¾ of the peak was collected, and the tail end of the peak was discarded.

In this fashion, 22.6 g of crude M—PEG—DMT 5000 was purified in 2 g portions to obtain 15.44 g of the title product.

EXAMPLE 5

Synthesis of Zero Diol Methoxypolyethylene Glycol from Dimethoxytrityl Methoxypolyethylene Glycol 10 g M—PEG—DMT 5000 was placed in a 500 ml flask and dissolved in 320 ml Milli-Q water. Sulfuric acid was added (80 ml) as a slow stream to bring the concentration to 20%. The solution turned red and homogeneous. After stirring overnight, the acid solution was extracted with 2×500 ml chloroform, and the combined extracts dried over MgSO$_4$, concentrated, and the red oil poured as a thin stream into 2 liters of anhydrous ether at 20° C. The precipitate was allowed to settle for 24 hours. It was collected in a course frit sintered glass funnel, and then washed with 2×200 ml portions of anhydrous ether. The precipitate cake was broken up and dried under vacuum to yield 8.68 g methoxy-PEG 5000 (zero diol).

EXAMPLE 6

Synthesis of Zero Diol Methoxypolyethylene Glycol Succinate from Zero Diol Methoxypolyethylene Glycol M—PEG—OH 5000 zero diol (4.7 g, 0.94 mmol) was dissolved in 100 ml toluene. The solution was brought to reflux and a Dean-Stark trap was used to remove any water. After 1 hour at reflux, a total of 80 ml toluene was removed by distillation, and the vessel containing 20 ml toluene, was allowed to cool under argon positive pressure. Succinic anhydride was added (110 mg, 1.1 mmol), followed by 4-dimethylaminopyridine (137 mg, 1.12 mmol). Since the succinic anhydride did not dissolve, 10 ml of anhydrous ethanol free chloroform was added, and the solution was held at a reflux using an oven dried condenser. After 15 h at reflux, the solution was cooled and then stirred with 10 g of cation exchange resin, filtered, and the filtrate concentrated to obtain the title compound.

EXAMPLE 7

Synthesis of Zero Diol Methoxypolyethylene Glycol Succinimidyl Succinate from Zero Diol Methoxypolyethylene Glycol Succinate A solution of M—PEG—succinate from Example 7 (4.15 g, 0.83 mmol) in 100ml of toluene was dried azeotropically. A portion of the toluene was distilled off (60 ml, leaving 40 ml in the reaction flask) and N-hydroxysuccinimide (100 mg, 0.87 mmol) was added, followed by the careful addition of 30 ml of ethanol free anhydrous chloroform. An additional 25 ml of the mixed solvent was removed by distillation and the solution was allowed to cool at room temperature under argon. DCC was added (200 mg, 9.7 mmol) and the solution was stirred. After 10 minutes, DCU began to crystallize out. After stirring for two days, an additional 25 mg (0.22 mmol) of N-hydroxy succinimide was added. The dicyclohexyl urea (DCU) slurry was filtered and the precipitate was washed with toluene. The filtrate was concentrated by rotary evaporation giving an additional precipitation of dicyclohexyl urea (DCU). The filtered concentrate was added dropwise into one liter of anhydrous ether. The precipitate was collected on a Whatman 9 cm 6 F/F glass fiber filter and then dried under high vacuum for 15 hours, to give 3.37 g of M—PEG—SS.

Active ester content: $1.71 \times 10^{-4}$ mol/g; HPLC indicated: 1.3% M—PEG—S; other impurities: 1.2%; DCU none detected; total impurity: 3%.

EXAMPLE 8

Synthesis of Zero Diol PEG—SOD

Superoxide dismutase (1.33 ml of 75 mg/ml stock) was added to 18.67 ml of reaction buffer (100 mM sodium phosphate, pH 7.8) and the solution was brought to 30° C. M—PEG—SS from Example 8 (300 mg) was added in one portion and the pH was maintained at 7.8 by use of a pH stat. After 28 minutes the reaction pH became unchanging and the sample was concentrated on Centrium centrifugal membrane of 10,000 MW cutoff. The concentrated sample was exchanged in this manner with Dulbecco's PBS which had been adjusted to pH 6.2 with 1M HCl. Five exchanges at a total of 60 ml were performed. Size exclusion HPLC showed negligable high MW peak indicating that the title compound contained negligable amounts of material derived from diol (i.e., it was "zero diol").

The following examples illustrate the preparation of other biologically active proteins covalently joined to PEG.

EXAMPLE 9

Synthesis of Low Diol Methoxypolyethylene Glycol-succinoyl-catalase 4.17 ml of an aqueous suspension of catalase containing 24.0 mg of protein per ml was diluted with 15.84 ml of 0.1M sodium phosphate buffer, pH 7.8. To this solution, magnetically stirred and heated to 30° C., was added 550 mg of low diol methoxy PEG—SS. The pH of the reaction mixture was maintained at 7.8 using a Mettler DL25 titrator programmed in the pH stat mode to add 0.5 normal sodium hydroxide solution as required. After 0.5 hour the reaction mixture was filtered through a 0.45 micron low protein binding polysulfone filter and placed in two Amicon Centriprep 30 Concentrators (30K NMWL membrane) and buffer was exchanged several times with Dulbecco's PBS. The retentate solution containing the low diol PEG-catalase was then filtered through a 0.2 micron filter. Conjugate formation was demonstrated by SEHPLC and gel electrophoresis.

EXAMPLE 10

Synthesis of Low Diol PEG-Ovalbumin 503 mg of ovalbumin (Sigma) was dissolved in 50 g of 0.25M, pH 7.8 phosphate buffer at room temperature in a polyethylene beaker containing a Telfon-coated magnetic stir bar. After stirring for 15 minutes, 1.900 g of low diol M—PEG(5,000)—SS was added all at once. The pH of the reaction mixture was controlled at 7.8 with a Mettler DL25 pH stat which added 0.5 N NaOH as needed. The reaction was allowed to continue for 1 hour at room temperature, and then the reaction mixture was diafiltered through an Amicon YM30 membrane using a stirred cell device operated under 25 psi of argon overnight in a refrigerator at 4° C. After 800 ml of buffer had beed diafiltered, the product was concentrated by ultrafiltration, filtered through a 0.2 micron polysulfone filter, and vialed in sterile glass vials to give 44.3 g of solution with a protein content of 10.5 mg/ml. The degree of protein modification was determined to be 71.4% by titration analysis of lysine amines.

EXAMPLE 11

Synthesis of Low Diol mPEG$_{5K}$-S-Ovalbumin 10 ml of a cold 10 mg/ml solution of ovalbumin (Sigma, grade VI) in 0.25M phosphate buffer, pH 7.4 was added to 382 mg of low diol mPEG$_{5K}$-SS and stirred at 5° C. for 16 hours. The product was purified in a Centriprep 30 Concentrator (Amicon, 30K NMWL membrane) using Dulbelco's PBS as the exchange buffer. The purified solution was filtered through a 0.2 μm filter to give 6.539 g containing 13.8 mg/ml of 74% modified (TNBS titration method) protein.

In a similar manner, 100 mg of ovalbumin was reacted with 283 mg of low diol mPEG$_{5K}$-SS giving 6.274 g containing 13.8 mg/ml of 74% modified protein.

In a similar manner, 100 mg of ovalbumin was reacted with 190 mg of low diol mPEG$_{5K}$-SS giving 5.704 g containing 16.8 mg/ml of 67% modified protein.

EXAMPLE 12

Synthesis of Low Diol mPEG$_{5K}$-S-rhu-IL4

190 μl of a 5.26 mg/ml solution of rhu-IL4 (Immunex) was diluted with 772 μl of 0.1M borate buffer, pH 8.5. The rhu-IL4 solution was then treated with 29.2 μl of a 34 mg/ml solution of low diol methoxy PEG—SS in DMF. After 1 hour and 20 minutes at room temperature the reaction mixture was centrifuged and injected directly onto a preparative SEHPLC column. The purified conjugate was shown to be essentially a single band on gel electrophoresis.

EXAMPLE 13

Synthesis of Low Diol mPEG$_{5K}$-S-NT

A solution containing 8.7 mg of neurotensin (NT) (BaChem) in 2.175 ml of 0.25M phosphate buffer, pH 7.8 was added to 174 mg of low diol mPEG$_{5K}$-SS. The reaction mixture was kept at room temperature for 1.75 hours, then refrigerated. Pure mono-mPEG$_{5K}$-S-NT was obtained after separation from NT—PEG$_{8K}$-NT by preparative reverse phase HPLC on a C-8 column eluting with a water/acetonitrile gradient.

The formulations of the present invention are made using conventional techniques known to those skilled in the art. Optionally, the formulation may contain sucrose or trehalose.

Specific formulations are illustrated in Table I.

TABLE I

| Example | PEG SOD (U/ml) | Phosphate Buffer (mM) | pH | HPCD % w/v | Sucrose % w/v |
|---------|----------------|----------------------|-----|------------|---------------|
| 14 | 25,000 | 10 | 6.2 | — | 5 |
| 15 | 50,000 | 10 | 6.2 | — | 5 |
| 16 | 75,000 | 10 | 6.2 | — | 5 |

TABLE I-continued

| Example | PEG SOD (U/ml) | Phosphate Buffer (mM) | pH | HPCD % w/v | Sucrose % w/v |
|---|---|---|---|---|---|
| 17 | 100,000 | 10 | 6.2 | — | 5 |
| 18 | 125,000 | 10 | 6.2 | — | 5 |
| 19 | 150,000 | 10 | 6.2 | — | 5 |
| 20 | 25,000 | 10 | 6.2 | — | 10 |
| 21 | 50,000 | 10 | 6.2 | — | 10 |
| 22 | 75,000 | 10 | 6.2 | — | 10 |
| 23 | 100,000 | 10 | 6.2 | — | 10 |
| 24 | 125,000 | 10 | 6.2 | — | 10 |
| 25 | 150,000 | 10 | 6.2 | — | 10 |
| 26 | 25,000 | 10 | 6.2 | — | 20 |
| 27 | 50,000 | 10 | 6.2 | — | 20 |
| 28 | 75,000 | 10 | 6.2 | — | 20 |
| 29 | 100,000 | 10 | 6.2 | — | 20 |
| 30 | 125,000 | 10 | 6.2 | — | 20 |
| 31 | 150,000 | 10 | 6.2 | — | 20 |
| 32 | 25,000 | 10 | 6.2 | 5 | — |
| 33 | 50,000 | 10 | 6.2 | 5 | — |
| 34 | 75,000 | 10 | 6.2 | 5 | — |
| 35 | 100,000 | 10 | 6.2 | 5 | — |
| 36 | 125,000 | 10 | 6.2 | 5 | — |
| 37 | 150,000 | 10 | 6.2 | 5 | — |
| 38 | 25,000 | 10 | 6.2 | 10 | — |
| 39 | 50,000 | 10 | 6.2 | 10 | — |
| 40 | 75,000 | 10 | 6.2 | 10 | — |
| 41 | 100,000 | 10 | 6.2 | 10 | — |
| 42 | 125,000 | 10 | 6.2 | 10 | — |
| 43 | 150,000 | 10 | 6.2 | 10 | — |
| 44 | 25,000 | 10 | 6.2 | 20 | — |
| 45 | 50,000 | 10 | 6.2 | 20 | — |
| 46 | 75,000 | 10 | 6.2 | 20 | — |
| 47 | 100,000 | 10 | 6.2 | 20 | — |
| 48 | 125,000 | 10 | 6.2 | 20 | — |
| 49 | 150,000 | 10 | 6.2 | 20 | — |
| 50 | 25,000 | 10 | 6.2 | 5 | 5 |
| 51 | 50,000 | 10 | 6.2 | 5 | 5 |
| 52 | 75,000 | 10 | 6.2 | 5 | 5 |
| 53 | 100,000 | 10 | 6.2 | 5 | 5 |
| 54 | 15,000 | 10 | 6.2 | 5 | 5 |
| 55 | 150,000 | 10 | 6.2 | 5 | 5 |
| 56 | 25,000 | 10 | 6.2 | 10 | 10 |
| 57 | 50,000 | 10 | 6.2 | 10 | 10 |
| 58 | 75,000 | 10 | 6.2 | 10 | 10 |
| 59 | 100,000 | 10 | 6.2 | 10 | 10 |
| 60 | 125,000 | 10 | 6.2 | 10 | 10 |
| 61 | 150,000 | 10 | 6.2 | 10 | 10 |
| 62 | 25,000 | 10 | 6.2 | 15 | 5 |
| 63 | 50,000 | 10 | 6.2 | 15 | 5 |
| 64 | 75,000 | 10 | 6.2 | 15 | 5 |
| 65 | 100,000 | 10 | 6.2 | 15 | 5 |
| 66 | 125,000 | 10 | 6.2 | 15 | 5 |
| 67 | 150,000 | 10 | 6.2 | 15 | 5 |
| 68 | 25,000 | 10 | 6.2 | 5 | 15 |
| 69 | 50,000 | 10 | 6.2 | 5 | 15 |
| 70 | 75,000 | 10 | 6.2 | 5 | 15 |
| 71 | 100,000 | 10 | 6.2 | 5 | 15 |
| 72 | 125,000 | 10 | 6.2 | 5 | 15 |
| 73 | 150,000 | 10 | 6.2 | 5 | 15 |

Formulations of the present invention are lyophilized using the following process.

Vials of required dimensions are chosen to be filled by a formulation based upon dose requirements. In choosing vials to accommodate a dose, the fill volume should not exceed the diameter of the vial. For example, a 5 ml fill should not be introduced into less than a 10 ml vial. After filling, the vials are loaded into the drying chamber and placed directly onto the refrigerated shelves which were pre-chilled to 4° C. Thermocouples are placed inside a number of the vials to monitor the temperature of the formulation during the lyophilization process. The vials are then allowed to equilibrate to the temperature of the shelves (4° C.) before lowering the shelves' temperature to −40° C. Once reaching −40° C., the vials are kept at this temperature for about 6 hrs to allow complete freezing of the formulation. After this time period the condenser coils are chilled to −80° C. and the vacuum pump is turned on to evacuate the condenser chamber followed by the process of primary and secondary drying. In the primary drying process, the main valve between the condenser and the drying chamber is opened and the drying chamber is evacuated to a pressure of about 100 microns with a nitrogen gas bleed. Upon reaching a pressure of 100 microns, the shelf temperature is raised to −20° C. to start the sublimation process. This portion of the lyophilization cycle requires about 10 to 18 hrs. The primary drying process is complete when all of the ice disappears from the frozen matrix and the thermocouple temperature has reached −20° C. In the secondary drying process, the temperature is raised from −20° C. to +25° C. to remove all the ice that was not removed during the lyophilization process. This removal required approximately 4 to 8 hrs.

After the completion of the secondary drying process the main valve is closed off and the drying chamber is filled with nitrogen so as to maintain a slight vacuum in the chamber. The stoppering ram is then activated and the closures are pushed down into the vials. The drying chamber is then equilibrated to atmospheric pressure and the chamber door is opened to remove the vials and apply the crimp seals. The vials then are stored at the prescribed temperature until reconstituted with water for injection.

Shelf-life of the formulations of the present invention were found to be excellent. Shelf-life is illustrated by the following comparative studies using reconstituted solutions to observe visual appearance of the formulations and Size Exclusion High Performance Liquid Chromatography (SEHPLC) to determine % high molecular weight (HMW) of material contained in the formulations shown in Examples 74 and 75.

Formulation A, according to the present invention, contained 10% HPCD.

Formulation B, for comparative purposes, contained 10% sucrose and no HPCD.

Both formulations contained 10 mM phosphate buffer at pH 6.2 and 75,000 U/ml PEG SOD. Fill volume of vials was 0.5 ml; temperature conditions were 4° C., 22° C., 30° C. and 50° C.; both formulations were lyophilized and maintained at the above temperatures for 30 months, and then reconstituted and tested as shown.

Example 74
Appearance of Reconstituted Formulations

| Formulation A | Appearance | Formulation B | Appearance |
|---|---|---|---|
| 4° C. | clear, blue-green | 4° C. | clear, blue-green |
| 22° C. | clear, blue-green | 22° C. | clear, blue-green |
| 30° C. | clear, blue-green | 30° C. | clear, blue-green |
| 50° C. | clear, blue-green | 50° C. | turbid, yellowish-brown |

HMW Determination Using SEHPLC

SEHPLC is performed by equilibrating a Shodex WS-803F column (0.8×30 cm) in 0.1M Phosphate Buffer, pH 6.5, 0.15M Sodium Chloride at 1 mL/min flow rate and pumped through a detector set at 280 nm. This column is capable of resolving differences in molecular weight based on its fractionation range and exclusion limit (greater than 1 million MW). Under these conditions, the high molecular weight material elutes before low molecular weight material (salts and small molecular weight components). The detector is connected to a computer that is programmed to integrate the peaks based on numerous parameters and quantify amount of the peaks based on a percent basis.

The % HMW species found and shown in Example 75 is a measure of the extent of polypeptide aggregation on storage. Example 75 also shows "Free Peg" (which is an indicator of the extent of hydrolysis of the succinate ester bond) and % enzyme activity.

Stability Studies with Lyophilized PEG-SOD Formulations Containing 10% Sucrose or 10% HPβCD at 2 and 10 Months Stored at Various Temperatures[1]

| Formulation (75,000 U/mg) | Temperature (°C.) | HMW[2] (%) 2 mo | HMW[2] (%) 10 mo | Free PEG[3] (mg/ml) 2 mo | Free PEG[3] (mg/ml) 10 mo | % Activity[4] 2 mo | % Activity[4] 10 mo |
|---|---|---|---|---|---|---|---|
| 10% Sucrose | 4 | 0.3 | 0.2 | 0.35 | 0.1 | 99 | — |
|  | 22 | 0.4 | 0.6 | 0.36 | 0 | 100 | — |
|  | 30 | 0.7 | 0.9 | 0.44 | 0 | 98 | 100 |
|  | 50 | 20 | >50 | 3.45 | ~10 | 71 | — |
| 10% HPβCD | 4 | 0.3 | — | 0.12 | — | 100 | — |
|  | 22 | 0.4 | — | 0.08 | — | 99 | — |
|  | 30 | 0.4 | 0.7 | 0.14 | 0.9 | 100 | 100 |
|  | 50 | 0.6 | 4.8 | 0.87 | 3.23 | 95 | 92 |

[1]Visual examination of the freeze dried cakes before reconstitution showed that the 50° C. sucrose formulation had discolored.
[2]HMW represents impurities such as polypeptide aggregates and is expressed as the % difference form control conditions (time).
[3]Free PEG represents the hydrolysis of the succinyl ester bond and is expressed as % difference from control conditions (time).
[4]Expressed as % of initial value.

As can be seen from the data in Example 75, the HPβCD formulation demonstrates excellent stability on storage at 30° C. No significant change in enzyme activity was seen even after 10 months of storage indicating that satisfactory stability of the enzyme is maintained. The marked superiority of HPβCD as a stability is evident by comparison of the % HMW values between the sucrose and the HPβCD formulations on 50° C. storage: the % HMW value for the HPβCD formulation after heat stressing at 50° C. for 10 months was only 4.8 as compared to >50 for the sucrose formulation under identical conditions. The dramatic stabilizing ability of HPβCD even under high temperature storage is indicative of a unique stabilizing mechanism afforded by this stabilizer that minimizes protein interaction and thus decreases the formation of HMW species. It may be theorized that since cyclodextrin structurally contains cavities, it is probable that the protective mechanism is related to encapsulation of certain reactive centers (associated with the formation of HMW aggregates) which minimizes interaction and minimizes aggregation.

The enhanced stability afforded by the present invention permits storage of the product at room temperature and increases its shelf-life. This lyophilized product is suitable for packaging in either a conventional glass vial or in a prefilled syringe. The prefilled syringe offers a "ready to use" product that requires minimal handling and is well suited for emergency use. The formulations have great utility heretofore not provided, in clinical, hospital and emergency situations.

While preferred embodiments of the invention have been described and illustrated in the specification, it is to be understood that such is merely illustrative of the underlying concept and features of the invention and are not to be limiting of the scope of the invention and the appended claims.

What is claimed is:

1. A method of treating a disease condition caused by superoxide anions on tissue in a mammal comprising administering an effective amount of a composition comprising from about 150 to about 150,000 units/ml of a covalently bound low diol polyethylene oxide superoxide dismutase:

from about 0.1 to about 20% w/v of cyclodextrin: and from about 0.01 to about 50 nM buffer, said composition having a pH of from about 5.7 to about 6.5.

2. A method of treating a disease condition caused by superoxide anions on tissue in a mammal comprising administering an effective amount of a composition comprising:

from about 150 to about 150,000 units/ml of a covalently bound low diol polyethylene oxide bovine superoxide dismutase:

from about 0.1 to about 20% w/v of cyclodextrin; and from about 0.01 to about 50 nM buffer, said composition having a pH of from about 5,7 to about 6.5.

3. The method of claim 1 wherein said disease condition is inflammation.

4. The method of claim 1 wherein said disease condition is ischemia.

5. The method of claim 1 wherein said disease condition is reperfusion injury.

6. The method of claim 1 wherein said disease condition is trauma.

7. The method of claim 2 wherein said disease condition is inflammation.

8. The method of claim 2 wherein said disease condition is ischemia.

9. The method of claim 2 wherein said disease condition is reperfusion injury.

10. The method of claim 2 wherein said disease condition is trauma.

* * * * *